United States Patent [19]

Melnick et al.

[11] 4,277,250

[45] Jul. 7, 1981

[54] METHODS FOR DETECTING AND QUANTIFYING OCCULT BLOOD

[75] Inventors: Joseph L. Melnick; Craig Wallis, both of Houston, Tex.

[73] Assignee: Baylor College of Medicine, Houston, Tex.

[21] Appl. No.: 101,722

[22] Filed: Dec. 10, 1979

[51] Int. Cl.³ .............................................. G01N 33/72
[52] U.S. Cl. .................................... 23/230 B; 23/913; 23/931; 23/932; 435/28; 435/272
[58] Field of Search ........................ 23/230 B, 913, 931, 23/932; 435/28, 805, 808, 810, 272, 4

[56] References Cited

U.S. PATENT DOCUMENTS

| | | | |
|---|---|---|---|
| 3,350,174 | 10/1967 | Mattenheimer | 23/913 X |
| 3,919,044 | 11/1975 | Melnick et al. | 435/272 X |
| 4,066,512 | 1/1978 | Lai et al. | 435/4 X |
| 4,138,214 | 2/1979 | Givner | 23/230 B |
| 4,142,856 | 3/1979 | Acuff | 23/230 B |
| 4,200,690 | 4/1980 | Root et al. | 435/28 X |

*Primary Examiner*—Arnold Turk

*Attorney, Agent, or Firm*—Watson, Leavenworth, Kelton & Taggart

[57] ABSTRACT

A method for detecting occult blood in aqueous samples of human specimens, particularly aqueous suspensions of fecal matter is disclosed. The method comprises acidifying an aqueous test sample, which in the case of fecal matter has been treated with lysozyme to clear the suspension; separating the liquid and solid portions of the test sample and passing the acidified liquid portion through an electro-negatively charged membrane; thereafter removing residual test liquids from the membrane; treating the membrane with a peroxidase indicator and observing the development of color on the treated membrane surface. A method for quantifying occult blood is also disclosed which comprises subjecting an aqueous sample to the disclosed detection method and comparing the color developed with a standardized scale reflecting colors developed by treating samples containing known incremental quantities of hemoglobin in accordance with the detection method of the invention.

19 Claims, No Drawings

METHODS FOR DETECTING AND QUANTIFYING OCCULT BLOOD

BACKGROUND OF THE INVENTION

1. Field of the Invention

This invention relates to methods for detecting and quantifying occult blood employing a peroxidase indicator.

2. Description of the Prior Art

Detection of occult blood in stool samples may lead to the early diagnosis of colon cancer. Colorectal cancer detected in asymptomatic patients is usually localized without involvement of lymph nodes. When detection is delayed until the symptomatic stage, lymph node involvement is found in approximately 40% of the cases. Those patients receiving the benefits of early diagnosis have a 30% better survival chance as compared to those patients who have a late diagnosis.

Hemoglobin, being a peroxidase, can be detected and quantified by means of a peroxidase indicator comprising a reduced or decolorized dye and hydrogen peroxide. Peroxidases catalyze the decomposition of peroxide to water and oxygen. The liberated acceptor oxygen oxidizes the reduced indicator dye, whereby the color of the oxidized state is developed. There is a direct relationship between color intensity developed and peroxide decomposition which is in turn related to the amount of peroxidase present in a sample. By measuring color intensity, as by measuring absorbance at the optional wavelength, quantification of a peroxidase is possible.

Thus, occult blood may be detected using colorimetric tests based on the reaction of hemoglobin with a peroxidase indicator, such as hydrogen peroxide and either o-tolidine or gun guaiac. Other reagents have been described, but the o-tolidine and guaiac tests are commercially available and have been used in detection of occult blood. Occult blood tests in common use include preparations of gum guaiac (City Chemical Corp., New York), dilute alcoholic solutions of guaiac (Tincture of guaiac; Harleco, Philadelphia), orthotolidine tablets (Hematest; Ames Co., Elkhart, Ind.), and a guaiac slide (Hemoccult; Smith, Kline and French Laboratories, Philadelphia). The reliability and sensitivity of these tests can be determined by measuring occult blood independently using $^{51}Cr$-labeled red blood cells.

Serious doubts have been raised about the reliability of some of these peroxidase indicator tests because of the high frequency of false-positives. Such misleading results lead to the unnecessary performance of additional expensive and uncomfortable diagnostic tests.

False-positives can be due to the presence in faces of peroxidases, other than hemoglobin, which can produce positive reactions. Plant peroxidases, chlorophyl and animal hemoglobin and myoglobin may survive digestion and produce a positive reaction. Intestinal bacteria may also produce peroxidases. Other false-positive results can occur because of the ingestion of certain foods, e.g., bananas, red meat, and iron.

False-positives are avoided by some of the currently employed peroxidase indicator tests at the expense of sensitivity. Diminished sensitivity to occult blood, though effective to reduce false-positives, results in false-negatives which delay diagnosis. False-negatives may also be due to the presence of Vitamin C in feces.

Erroneous results with present colorimetric peroxidase tests can also be caused by the pigment in feces which blends with the color of the peroxidase indicator dye. Further, reducing agents present in feces may interfere with the action of the peroxidase.

The commercially available peroxidase indicator preparations for detection of occult blood are all semi-quantitative. That is, they yield results that are expressed as 0, +, ++, etc. Quantification, such as is available with detection using $^{51}Cr$-labeled cells, is not possible. The semi-quantitative nature of the results appears to be the result of the action of an inhibitor of hemoglobin activity in stool. The inhibitor is effective at high dilutions of stool in water, and its effects are completely eliminated only at a dilution of 1:8,000. Blood is detected only when it is present in excess of the inhibitor demand. Since this may occur at blood levels where prognosis is poor, these inhibitors reduce sensitivity, as well as prevent quantitative measurement.

The presence of an inhibitor of the peroxidase reaction in urine also interferes with detection and precludes exact quantification of myoglobin or hemoglobin. As with stool, readings for the presence of blood are reported on a 0 to ++++ scale.

The effects of the inhibitor can be overcome by using an excess if substrate, either chromogen or peroxide. As high concentrations of peroxide reduce hemoglobin activity, excess dye may be added. Although this permits detection of hemoglobin in urine or stool, the variable amount of inhibitor present makes exact quantification impossible.

Therefore, a need exists for methods of detecting occult blood which are sensitive enough to reliably detect small amounts of hemoglobin while discriminating against other peroxidases. Further, a need exists for an accurate colorimetric test for quantitatively detecting occult blood, so that by following serial fecal samples, it is possible to determine whether the bleeding is adventitiously present or is increasing in volume.

SUMMARY OF THE INVENTION

In accordance with the invention a method for detecting occult blood in human specimens is provided which comprises:

(a) acidifying a liquid test sample of the specimen with an organic acid;

(b) separating the liquid portion of the test sample from the solid portion;

(c) passing the acidified liquid portion through an electronegatively charged membrane;

(d) thereafter, washing the membrane surface to remove residual test sample liquids;

(e) treating the washed surface with a peroxidase indicator composition suitable for detecting hemoglobin; and (f) observing the color of the washed membrane surface.

In addition, quantitative detection of occult blood in a specimen is effected by comparing the color of the membrane resulting from treatment of the sample in accordance with steps (a) through (f) with a standardized color guide.

The invention has particular application to detection and quantification of occult blood in fecal material. Fecal specimens may be prepared for treatment in the process by suspending feces in an aqueous buffer solution and treating the resulting suspension with lysozyme.

DETAILED DESCRIPTION OF THE INVENTION

This invention provides an improved method for detecting occult blood in human specimens, such as feces and urine. In the practice of the invention, occult blood is detected by means of a peroxidase indicator composition, which produces a color response in the presence of peroxidases, such as hemoglobin. By providing means for eliminating the effects of substances which interfere with the peroxidase action of hemoglobin, the process of the invention provides a highly sensitive, reliable colorimetric peroxidase indicator test, which is selective with respect to hemoglobin in occult blood. The invention further provides means for quantitatively assessing the hemoglobin in a specimen.

In broad terms the method of the invention comprises separating the hemoglobin in a specimen from those substances which compete or interfere with the peroxidase activity of the hemoglobin. The separated hemoglobin is thereupon contacted with a peroxidase indicator composition, a color change of which accurately indicates the presence of hemoglobin. Moreover, the intensity of the color change reflects the relative amount of the hemoglobin in the specimen.

More specifically, the invention provides a method for detecting the presence of occult blood in a human specimen, which comprises acidifying a test sample of the specimen, separating the liquid and solid portions of the samples and passing the acidified liquid portion through an electro-negatively charged membrane, washing residual sample fluids from the membrane surface and thereupon contacting the washed surface with a peroxidase indicator composition. Ripening of the chromogen in the indicator composition manifests the presence of hemoglobin.

The degree of chromogen ripening is a measure of the amount of hemoglobin in the sample which in turn is directly related to the amount of occult blood in the specimen. Thus by comparison of the intensity of colors resulting from treatment of different specimens in accordance with the method of the invention, assessment of the relative amounts of occult blood in the specimens is possible. Actual quantification of the occult blood in a test specimen may be achieved by comparing the color resulting from treatment of the test specimen with a standard color guide, which has been developed by subjecting samples of specimens containing known amounts of hemoglobin to the detection method of the invention. The present invention has particular application to detection and quantification of occult blood in human specimens, such as fecal matter and urine.

For purposes of the present invention, the hemoglobin of a specimen must be dissolved in a relatively clear aqueous solution at the time of treatment. Where the specimen to be analyzed is fecal matter, suspension of feces in an aqueous solution followed by treatment with an enzyme produces an aqueous sample suitable for treatment in accordance with the invention.

An acceptable fecal suspension can be produced employing an aqueous buffer solution, such as an aqueous glycine solution. The feces may be suspended in the solution by simply shaking with the solution in a closed test tube until a homogenous suspension is produced. Any other means which is effective to create a homogeneous suspension may also be employed. About 1% fecal suspensions are preferred for use in the practice of the present invention. Such suspensions may be formed by combining 10 mg of feces with each ml of diluents.

The presence of certain materials, such as bacterial fragments, interfere with further processing of the fecal suspension in accordance with the method of the present invention. Specifically, certain materials in fecal suspensions produce a turbid supernatant upon centrifugation of the suspension and/or clog filters thus preventing ready separation and concentration of the dissolved hemoglobin. Digestion of these interfering substances by means of enzymes has been found to result in aqueous samples of fecal matter which are readily processed in accordance with the invention. The interfering substances consist in large measure of polysaccharides and thus an enzyme specific for polysaccharides must be employed. Lysozyme is a particularly suitable enyzme for this purpose. Efficient digestion of interfering substances in a 1% fecal suspension can be achieved by treatment of the suspension with about 1 mg/ml of lysozyme for about 5-15 minutes at about pH 8 and 37° C. The hemoglobin content of suspensions treated in this manner may readily be analyzed by means of the method of the invention.

Urine specimens do not require suspension and digestion prior to analysis in accordance with the invention. The hemoglobin is dissolved in the urine, which is itself a suitable aqueous solution for analysis by means of the present invention.

For purposes of the present invention, it is to be understood that references to test samples denote aqueous solutions containing the hemoglobin of the specimen, which have sufficient clarity to permit ready separation and concentration of the hemoglobin in accordance with the invention. Such samples may comprise the specimen itself or may be solutions derived from the specimen, such as the above described enzyme treated fecal suspensions.

In the practice of the invention, the test sample of the specimen is acidified, in order to enhance adsorption of hemoglobin to electronegative membranes. Although inorganic acids will to some degree enhance hemoglobin adsorption, organic acids are much more efficient acidifiers. Acetic acid and citric acid are both suitable organic acids for this purpose.

The concentration of acid in the test sample affects the degree of hemoglobin adsorption. Test samples which contain between 0.1% and 10% organic acid exhibit substantial hemoglobin adsorption to electronegative membranes. Optimum results are obtained with samples containing 1% organic acid. Excess amounts of acid should be avoided since the hemoglobin is adversely affected.

In a preferred mode of operation, the test sample is acidified and thereupon the liquid portion of the acidified sample is clarified by separation from the solid portion using liquid-solid separation techniques. Clarification may, however, be effected prior to acidification.

Centrifugation and filtration are effective separation techniques for use in the present method. Centrifugation at about 3000 rpm for about 5-15 minutes on a clinical centrifuge produces an adequately clarified test liquid. Preferably, however, clarification is accomplished by means of electropositive filters. About 0.65 to 2.0 micron electropositive filters give results comparable to centrifugation while simplifying and shortening the clarification procedure.

Following clarification, the hemoglobin in the test sample is concentrated on a membrane surface. This is accomplished by passing the clarified liquid through a filter capable of adsorbing the hemoglobin. Electronegative filters having a porosity of about 1 micron have been found effective hemoglobin adsorbents in the practice of the present invention. Specifically 1 micron electronegative Amerace, Millipore, Filterite and Cox filters may be employed.

Although many electronegative filter surfaces are capable of adsorbing hemoglobin, a number of filters contain naturally occurring, non-biological peroxidases which will react with the peroxidase indicator system and yield false-positive results. For purposes of this invention, hemoglobin adsorbents are to be understood to include those adsorbents which contain small amounts of non-biological peroxidases and which reproducibly give negative results in tests with hemoglobin free test specimens when treated in accordance with the invention. The 1 micron Amerace filter is a particularly suitable hemoglobin adsorbent. The other above-mentioned filters contain slightly higher concentrations of non-biological peroxidases than the Amerace filter. However, these other filters still give satisfactory results in the practice of the present invention, since with hemoglobin free liquid test samples background color levels are so low that they are read as negative for the presence of occult blood.

Following deposition of the hemoglobin on the membrane, the membrane surface is washed to remove residual test fluids. The washing is generally effected by passing small amounts of aqueous organic acid solution through the filter one or more times. A 1% acetic acid solution is an acceptable washing agent.

The presence of hemoglobin on the washed membrane may thereupon be detected by treating the membrane surface with a peroxidase indicator composition capable of detecting hemoglobin. After about 2–5 minutes the color of the filter is observed. If chromogen ripening is evident, the presence of hemoglobin is indicated. The absence of color indicates the absence of hemoglobin.

Peroxidase indicator compositions commonly comprise decolorized or reduced dye and hydrogen peroxide. For purposes of the present invention, a preferred composition comprises orthotolidine and hydrogen peroxide. Preferably equal volumes of 2% hydrogen peroxide and 0.5% orthotolidine (i.e., 5 mg/ml o-tolidine), are combined to form the indicator composition.

The degree of chromogen ripening is directly related to the amount of hemoglobin on the filter. Thus the intensity of the color developed is a measure of the quantity of hemoglobin in the test sample. The exact quantity of hemoglobin is determinable by comparison with a standarized color guide or chart.

A standardized chart for use in quantifying the amounts of hemoglobin in test samples can be produced by subjecting a series of samples containing known amounts of hemoglobin to the hemoglobin detection method of the invention. By testing a series of samples containing incrementally increasing amounts of hemoglobin under identical conditions and imprinting the resulting colors on a chart, a graded color guide for use as a standard in quantifying hemoglobin in the test samples can be created. In order to maximize the accuracy of hemoglobin quantification in accordance with the method of invention, the reagents and conditons employed to analyze the test sample should correspond as closely as possible to those employed in producing the graded standard.

A preferred mode of operation for analyzing hemoglobin content in fecal matter in accordance with the invention comprises the following sequence of steps.

The fecal matter is prepared for analysis by adding 100 mg feces to 10 ml of stock buffer solution. The buffer solution comprises 100 mg lysozyme powder, 375 mg glycine and 75 mg bicarbonate dissolved in sufficient distilled water to give a 100 ml solution. This stock buffer solution has a pH of 8.0–8.5, contains 1 mg/ml lysozyme and is 0.05 M glycine. The feces and buffer solution are mixed vigorously to produce a homogeneous suspension. The resulting test sample is then placed at 37° C. for 15 minutes. Immediately thereafter 1 ml of 10% glacial acetic acid is added to the tube. Thereupon the acidified fecal suspension is clarified.

Clarification is effected by passing the test sample through a plastic assembly which allows serial processing through a clarifier and a hemoglobin adsorbent. The assembly comprises a 25 mm, 2 micron electropositive Finite filter mounted into a plastic holder seated on the upper end of a hollow barrel, the lower end of which is in fluid tight engagement with the hemoglobin adsorbent. Three ml of fecal test sample are added to the reservoir of the clarifier assembly. Suction is applied whereby the sample is drawn through the clarifier and thence through the hemoglobin adsorbent. According to a most preferred practice the adsorbent is an electronegatively charged Amerace A-30 filter.

Processing through the clarifier assembly and adsorbent may be facilitated by employing an instrument which will seal the filter against the lower end of the clarifier barrel assembly and which has means for creating suction and drawing the filtrate into a waste reservoir.

After the sample is filtered through the hemoglobin adsorbent, the adsorbent is washed to remove residual fecal fluids, by drawing 5 ml of 1% acetic acid therethrough. One ml of indicator composition is then added to and immediately drawn through the hemoglobin adsorbent. After 2–5 minutes, the ripened color on the filter surface is observed and, if quantitative results are desired is compared to a standard color guide. In the event the color intensity on the filter surface of a test sample is greater than the highest value shown on a color guide, the test may be repeated with 10 fold more dilute test sample, in which event the quantity reflected by the matching color of the guide is multiplied by 10 to give the amount of hemoglobin in the test sample.

A standard color guide may be prepared by subjecting fecal samples containing known incremental amounts of hemoglobin to the same steps above outlined for test samples. The gradations of colors developed by this means can be used to provide a standard color guide for quantitative analyses. The color guide may, if desired, be mounted on a test card in which the hemoglobin adsorbent has been inlaid.

The following examples are illustrative of the invention:

EXAMPLE 1

In the below-described clinical tests the following materials and procedures were employed in the practice of the present invention:

Lysozyme-Buffer: Lysozyme, glycine and bicarbonate were ball-milled, and a mixture of 100 mg lysozyme powder, 375 mg Glycine and 75 mg bicarbonate were capsuled. One capsule was emptied into a 100 ml container, and distilled water was added to make a 100 solution. This diluted stock contained 1 mg/ml lysozyme and 0.05 M glycine and had a final pH of 8.0–8.5.

Fecal test sample: A plastic miniature spoon was provided which filled with fecal matter contains about 100 mg feces. The spoon containing the feces was placed into a screw capped tube and 10 ml of the buffer solution described above was added to the tube, which was then capped, and vigorously shaken to make a homogeneous suspension of the fecal matter. The sample was then held at 37° C. for 15 minutes, and immediately thereafter 1 ml of 10% glacial acetic acid was added to the tube. The acidified fecal suspension was then clarified as described below.

Clarification: A 25 mm, 2 micron electropositive Finite filter was mounted into a plastic holder seated in the upper part of a hollow barrel, the lower end of which was in fluid tight engagement with the hemoglobin adsorbent. Three ml of fecal test sample were added to the reservoir of the clarifier assembly. Suction was applied whereby the sample was drawn through the clarifier and thence through a 10 mm diameter area of the hemoglobin adsorbent.

Hemoglobin adsorbents: Electronegatively charged Amerace A-30 filters were used as the hemoglobin adsorbent.

Wash: The hemoglobin adsorbent was then washed twice with 5 ml 1% acetic acid to remove residual fecal fluids, by drawing the acid through the adsorbent.

Peroxidase indicator: One part by volume of 5 mg/ml o-tolidine to one part by volume 2% hydrogen peroxide was used as the indicator composition.

Peroxidase assays: One ml of indicator composition was added to and immediately drawn through the 10 mm diameter treated area of the hemoglobin adsorbent. After 2–5 minutes, the ripened color on the filter surface was observed and compared to a color guide.

Standardized Color Guide: Known amounts of hemoglobin were added to pooled, normal 1% fecal suspensions in glycine buffer at pH 8 containing 1 mg/ml lysozyme. Samples were held at 37° C. for 15 minutes and then a final of 1% acetic acid was added to each sample. The samples were then centrifuged at 3000 rpm for 15 minutes and 3 ml of each supernatant sample was filtered through a 10 mm diameter area of an Amerace A-30 hemoglobin adsorbent. Each adsorbent was washed twice with 5 ml (each wash) 1% acetic acid to remove residual fecal suspension from the filter. The 10 mm diameter treated surface of each adsorbent was treated with 1 ml peroxidase indicator which was immediately drawn through the hemoglobin adsorbent. After 2–5 minutes or chromagen ripening, the degree of color on the adsorbent surface was photographed. A color print was made of each result and imprinted upon a card, whereby a graded color chart was produced.

Results:

Fecal samples of ten volunteers who had no history of gastrointestinal disease were evaluated using the methods of the invention as described above. Evaluation of the fecal samples with the guaiac test and hemocult test were also carried out in accordance with the manufacturers' instructions. The results of these evaluations were as follows:

| Test | Positive | Negative |
| --- | --- | --- |
| Guaiac | 4 | 6 |
| Hemocult | 1 | 9 |
| Present Invention | 0 | 10 |

The fecal matter from the 10 volunteers was treated with a small amount of iron as found in vitamin supplements (10 mg/gram of feces), and the tests repeated as described above. The results were as follows:

| Test | Positive | Negative |
| --- | --- | --- |
| Guaiac | 10 | 0 |
| Hemocult | 7 | 3 |
| Present Invention | 0 | 10 |

The fecal matter from the above 10 volunteers was treated with hemoglobin a final of 1 mg/gram of feces. The tests were repeated as described above and gave the following results:

| Test | Positive | Negative |
| --- | --- | --- |
| Guaiac | 3 | 7 |
| Hemocult | 2 | 8 |
| Present Invention | 10 | 0 |

It should be noted that the positive results with the Guaiac and Hemocult tests are no greater in these samples than in the samples described above which did not contain added hemoglobin.

Duplicate samples of hemoglobin-treated fecal matter described above were also treated with ascorbic acid (10 mg/gram of feces) and the tests were repeated with the following results:

| Test | Positive | Negative |
| --- | --- | --- |
| Guaiac | 0 | 10 |
| Hemocult | 0 | 10 |
| Present Invention | 10 | 0 |

EXAMPLE 2

A gastrointestinal patient with a bleeding gastric ulcer provided a sample of feces which processed as described in Example 1. Since the present invention only detects freshly released colonic blood, the results of this test were negative. The guaiac test was weakly positive and the hemocult test was also weakly positive.

EXAMPLE 3

A gastrointestinal patient acutely ill with a bleeding colonic ulcer (based on radiological diagnosis) provided a sample of feces which was processed as described in Example 1. Column purification studies of this fecal matter required over 3 hours of processing and indicated that there was 2.5 mg occult blood/gram of feces. A positive value of 2.0 mg blood/gram of feces was obtained when the present detection method was employed and the result thereof compared with a standard. The Guaiac and Hemocult tests were negative.

EXAMPLE 4

Method for processing urine samples: No lysozyme-buffer solution was used. Undiluted urine was treated with acetic acid to give a final concentration of 1%. The clarifier used was a 0.65 micron Finite Filter, to remove bacteria which have peroxidases. Three ml of the urine containing acetic acid was added to the reservoir of the clarifier barrel. Employing the materials and methods described in Example 1, the sample was drawn through the clarifier and hemoglobin adsorbent; and the adsorbent was treated with acetic acid wash and indicator.

Urine samples, from 10 volunteers who were apparently normal, were tested for the presence of peroxidase according to the above-described procedure. All results were negative.

EXAMPLE 5

Six patients were evaluated to determine whether or not they were excreting peroxidases (hemoglobin or myoglobin) in their urine. The tests were conducted as described in Example 4. The color of the adsorbent was compared with a standard. The results were available to the physician within two minutes after receipt of the samples. These results and the final diagnosis are indicated below:

| Patient' tentative Diagnosis | Test Results (mg/100 ml) | Final Diagnosis |
| --- | --- | --- |
| Rheumatoid Arthritis | 0 | Same |
| Bacteriuria | 20 | E. coil Infection |
| Chest Pains | 50 | Died-Myocardial Infarction |
| Possible Infarct | 10 | Myocardial Infarction |
| Chest Pains | 0 | Hiatal hernia |
| Indigestion | 0 | Gastritis |

Although the values shown cannot be identified as hemoglobin or myoglobin, the screening did immediately indicate that further evaluation was required.

EXAMPLE 6

In order to evaluate the adsorption of hemoglobin to various filters in the practice of the present invention the following tests were conducted.

Three ml samples of 0.05 Glycine treated with hemoglobin to yield about 0.500 absorbance at 630 nm after 1 minute were treated with the final concentration of acid indicated. The samples were thereupon passed through the filters indicated (−, negatively charged filter; and + positively charged). All filters were about 1 micron porosity. The filtrates were assayed for unadsorbed hemoglobin by addition of 1 ml of the peroxidase indicator described in Example 1 to the 3 ml filtrate samples and after 1 minute measuring the absorbance at 630 nm. The results of these tests are set forth in Table 1.

TABLE 1

| HEMOGLOBIN DILUENT (final Conc. acid) | ABSORBANCES AT 630 nm | | | | |
| --- | --- | --- | --- | --- | --- |
| | Unfiltered Control | Amerace (−) Filtrate | Filterite (−) Filtrate | Cox (−) Filtrate | Finite (+) Filtrate |
| Saline-glycine Buffer (pH 6-7) | 0.520 | 0.160 | 0.120 | 0.180 | 0.450 |
| Acetic acid 10% | 0.410 | 0.000 | 0.000 | 0.000 | 0.400 |
| Acetic acid 1% | 0.510 | 0.000 | 0.000 | 0.000 | 0.510 |
| Acetic acid 0.1% | 0.530 | 0.090 | 0.070 | 0.120 | 0.480 |
| Citric acid 10% | 0.350 | 0.000 | 0.000 | 0.000 | 0.310 |
| Citric acid 1% | 0.450 | 0.000 | 0.000 | 0.000 | 0.400 |
| Citric acid 0.1% | 0.510 | 0.080 | 0.100 | 0.060 | 0.290 |
| HCL 1% | 0.060 | — | — | — | — |
| HCL 0.1% | 0.290 | — | — | — | — |
| HCL 0.01% | 0.450 | 0.080 | 0.000 | 0.000 | 0.140 |
| HCL 0.001% | 0.530 | 0.120 | 0.130 | 0.090 | 0.080 |
| Sulfuric Acid 0.1% | 0.200 | — | — | — | — |
| Sulfuric Acid 0.01% | 0.320 | — | — | — | — |
| Sulfuric Acid 0.001% | 0.490 | 0.090 | 0.020 | 0.040 | 0.090 |

These experiments reveal that hemoglobin added to glycine buffer solutions is efficiently adsorbed to electronegative filter surfaces only if the buffer is acidified with organic acids. The efficiency of hemoglobin adsorption to the filter surface is related to the type and concentration of acid used. Acetic acid and citric acid were more efficient acidifiers than inorganic acids. Excess inorganic or organic acids added to hemoglobin solutions deleteriously affected the hemoglobin. The results with electropositively charged filter surfaces indicate the inefficiency of these filter surfaces to adsorb hemoglobin.

EXAMPLE 7

Experiments were conducted to determine the influence of enzymes on the suspended matter in fecal suspensions. An excess (10 mg/ml) of pronase, pancreatin, trypsin or lysozyme was added to respresentative fecal suspensions. After 30 minutes at 37° C. and pH 8, the samples were centrifuged at 3000 rpm (clinical centrifuge) and the supernatant fluids were evaluated for clarity as measured at 540 nm.

Only the lysozyme manifested a clear supernatant.

EXAMPLE 8

The effects of lysozyme treatment on the turbidity of the liquid portion of fecal suspensions was evaluated by treating 3 ml samples of 1% fecal matter in 0.05 M glycine at pH 8 and 37° C. with the final concentrations of lysozyme indicated for the times indicated. Samples were immediately centrifuged at 3000 rpm for 5 minutes, and supernatants were assayed for turbidity by measuring absorbance at 540 nm. The results are set forth in Table 2.

TABLE 2

| Lysozyme Concentration (mg/ml) | ABSORBANCE Incubation Time at 37° C. | | |
| --- | --- | --- | --- |
| | 5 Min | 15 Min | 30 Min |
| None | 0.850 | 0.820 | 0.850 |
| 0.25 | 0.760 | 0.730 | 0.700 |
| 0.5 | 0.640 | 0.320 | 0.250 |

TABLE 2-continued

| Lysozyme Concentration (mg/ml) | ABSORBANCE Incubation Time at 37° C. | | |
|---|---|---|---|
| | 5 Min | 15 Min | 30 Min |
| 1.0 | 0.140 | 0.080 | 0.060 |
| 2.0 | 0.090 | 0.065 | 0.060 |
| 4.0 | 0.090 | 0.060 | 0.060 |

Example 9

The relative effectiveness of centrifugation and various filter means for separating the solid and liquid portions of test samples in the practice of the invention were evaluated. Four ml of hemoglobin was added to 100 ml of a 1% fecal suspension at pH 8 containing 1 mg/ml lysozyme. A duplicate sample without hemoglobin was used as a control. All samples were held at 37° C. for 15 minutes and then 3 ml samples were passed through a 25 mm clarifier or centrifuged at 3000 rpm as indicated in Table 3. Supernatant fluids from the centrifugation or the clarified filtrates were then passed through a hemoglobin adsorbent, the adsorbent was washed with acetic acid, and treated with 1 ml indicator as described in Example 1. The mg hemoglobin per gram feces in the control and test samples was then determined by comparing the color impregnated into the filter surface with the color guide which expressed the results as mg hemoglobin per gram feces.

Duplicate samples were tested only for turbidity after clarification by measuring percent transmission at 540 nm.

The results of these tests are set forth in Table 3.

TABLE 3

| CLARIFYING PROCESS | ABSORBANCE at 540 nm | mg HEMOGLOBIN/ Test Sample | gm FECES Control |
|---|---|---|---|
| None | 0.910 | Filter Clogged | |
| Centrifugation | 0.065 | 4.0 | 0.0 |
| 5 Micron Finite Clarifier | 0.160 | 6.0 | 1.5 |
| 2 Micron Finite Clarifier | 0.070 | 4.0 | 0.0 |
| 1 Micron Finite Clarifier | 0.065 | 4.0 | 0.0 |
| 0.65 Micron Finite Clarifer | 0.060 | 3.0 | 0.0 |

The results of these experiments indicate that the use of 1 or 2 Micron Finite Clarifiers is preferable. By their use a 5 second process can replace a more cumbersome centrifugation process which may require as much as 15 minutes.

The false positive resulting from the use of a 5 micron clarifier with the control sample represents a naturally occurring non-hemoglobin peroxidase, such as a vegetable or bacterial peroxidase. Such false positives can be avoided by use of clarifiers of less than 5 microns in the practice of the invention.

What is claimed is:

1. A method for detecting occult blood in a human specimen which comprises:
   (a) acidifying a liquid test sample of the specimen with an organic acid;
   (b) separating the test sample into a liquid portion and a solid portion;
   (c) passing the acidified liquid portion through an electronegatively charged membrane capable of adsorbing hemoglobin;
   (d) thereafter, washing the membrane surface to remove residual test sample liquids;
   (e) treating the washed surface with a peroxidase indicator composition suitable for detecting hemoglobin; and
   (f) observing the color on the treated membrane surface.

2. The method of claim 1 wherein the test sample comprises urine.

3. The method of claim 1 wherein the specimen comprises fecal matter.

4. The method of claim 3 wherein the test sample comprises a fecal suspension clarified by means of an enzyme capable of digesting polysaccharides.

5. The method of claim 3 wherein the test sample of the fecal matter is a 1% suspension of feces in aqueous glycine buffer diluent which suspension has been treated with lysozyme to clear the suspension.

6. The method of claim 5 wherein the treatment with lysozyme is effected at about pH 8 and 37° C. for about 5-15 minutes.

7. The method of claim 5 wherein about 1 mg of lysozyme is employed per ml of suspension.

8. The method of claim 1 wherein the organic acid is added to the sample to produce a final acid concentration of about 1%.

9. The method of claim 1 wherein the organic acid is citric acid.

10. The method of claim 1 wherein the organic acid is acetic acid.

11. The method of claim 1 wherein the test sample is separated into liquid and solid portions by centrifuging the acidified sample and decanting the resulting supernatant.

12. The method of claim 1 wherein the test sample is separated into liquid and solid portions by passing the acidified sample through an electropositive clarifier having a porosity of about 0.65 to about 2.0 microns.

13. The method of claim 1 wherein the electronegatively charged membrane has a porosity of about 1 micron.

14. The method of claim 1 wherein the membrane is washed with 1% acetic acid.

15. The method of claim 1 wherein the peroxidase indicator composition comprises o-tolidine and hydrogen peroxide.

16. The method of claim 15 wherein the composition comprises 1 part by volume of 2% hydrogen peroxide to each part by volume of 0.5% o-tolidine aqueous solution.

17. The method of claim 1 which further comprises quantifying the blood present in the specimen by comparing the color observed on the membrane surface with a color guide developed by subjecting samples containing known quantities of hemoglobin to the process of claim 1.

18. The method of claim 1 for detecting occult blood in fecal matter which comprises obtaining a liquid test sample by treating a 1% suspension of feces in aqueous glycine buffer with about 1 mg of lysozyme per ml of suspension at about pH 8 and 37° C. for about 5-15 minutes and performing steps (a) to (f) as follows:
   (a) acidifying the test sample resulting from the lysozyme treatment of the suspension by adding an organic acid to the sample to produce a final acid concentration of about 1%;
   (b) separating the acidified sample into a liquid and a solid portion by passing the test sample through an electropositive clarifier having a porosity of about 0.65 to 2.0 microns;

(c) passing the clarified filtrate through an electronegatively charged membrane capable of adsorbing hemoglobin;
(d) thereafter washing the membrane surface with 1% acetic acid to remove residual fecal fluids;
(e) treating the washed surface with a peroxidase indicator composition comprising o-tolidine and hydrogen peroxide; and
(f) observing the color on the treated membrane surface.

19. A method for quantitatively detecting the presence of occult blood in fecal matter which comprises subjecting a specimen of fecal matter to the process of claim 18 and thereafter comparing the color on the treated membrane surface with a standard reflecting the colors of known quantities of hemoglobin subjected to the process of claim 18.

* * * * *

UNITED STATES PATENT AND TRADEMARK OFFICE
CERTIFICATE OF CORRECTION

PATENT NO. : 4,277,250
DATED : July 7, 1981
INVENTOR(S) : Joseph L. Melnick, Craig Wallis It is certified that error appears in the above-identified patent and that said Letters Patent are hereby corrected as shown below:

Column 1, line 36, "gun" should read --gum--.

Column 1, line 53, "faces" should read --feces--.

Column 2, line 25, "if" should read --of--.

Column 3, line 65, "homogenous" should read --homogeneous--.

Column 5, line 53, "standarized" should read --standardized--.

Column 5, line 65, "conditons" should read --conditions--.

Column 7, line 51, "chromagen" should read --chromogen--.

UNITED STATES PATENT AND TRADEMARK OFFICE
CERTIFICATE OF CORRECTION

PATENT NO. : 4,277,250
DATED : July 7, 1981
INVENTOR(S) : Joseph L. Melnick, Craig Wallis It is certified that error appears in the above-identified patent and that said Letters Patent are hereby corrected as shown below:

Column 9, line 46, "Patient'" should read --Patients'--.

Column 9, line 50, "coil" should read --coli--.

Signed and Sealed this

Twenty-seventh Day of October 1981

[SEAL]

Attest:

GERALD J. MOSSINGHOFF

*Attesting Officer*  *Commissioner of Patents and Trademarks*